United States Patent [19]

Grove

[11] Patent Number: 4,783,221
[45] Date of Patent: Nov. 8, 1988

[54] COMPOSITIONS AND PROCESS FOR PRESERVING WOOD

[75] Inventor: Scott L. Grove, Lakewood, Ohio

[73] Assignee: Mooney Chemicals, Inc., Cleveland, Ohio

[21] Appl. No.: 940,548

[22] Filed: Dec. 12, 1986

[51] Int. Cl.⁴ .......................... C09D 5/16; B32B 21/04
[52] U.S. Cl. ................................ 106/18.22; 428/537.1
[58] Field of Search .................... 106/18.22; 428/537.1

[56] References Cited

U.S. PATENT DOCUMENTS

| | | | |
|---|---|---|---|
| 2,951,789 | 9/1960 | McCants | 106/18.16 |
| 3,761,488 | 9/1973 | Lewis et al. | 260/302 |
| 4,001,400 | 1/1977 | Hager | 424/134 |
| 4,150,026 | 4/1979 | Miller et al. | 260/299 |
| 4,193,993 | 3/1980 | Hilditch | 424/141 |
| 4,396,413 | 8/1983 | Miller et al. | 71/67 |
| 4,507,152 | 3/1985 | Collins et al. | 106/18.31 |

FOREIGN PATENT DOCUMENTS 2049430 5/1982 United Kingdom .

OTHER PUBLICATIONS

A. F. Preston et al., "Efficacy of N—Substituted Iosthiazolones for the Control of Wood Decay Fungi", 14 pages, 1984, Biodeterioration 6, in Press.

J. A. Dupont, "Selecting Fungicides", 6-page Publication, apparently a reprint of an article in *Modern Paint and Coatings*, Nov., 1978, a publication of Communication Channels, Inc.

Rohm and Haas publication, Trade Sales Coatings, "SKANE M-8, Paint Mildewcide", 10 pages, 1982.

Rohm and Haas publication entitled "Guidelines to Maximum Mildew Resistance Using SKANE M-8", 7 pages, 1972.

D. D. Nicholas et al., Document No. IRPG/WP/3306, International Research Group on Wood Preservation, May 28–31, 1984.

*Primary Examiner*—Theodore Morris
*Attorney, Agent, or Firm*—Renner, Otto, Boisselle & Sklar

[57] ABSTRACT

Novel compositions of matter and processes for utilizing such compositions in preserving wood are described. More particularly, the novel compositions comprise (A) at least one metal salt of an organic carboxylic acid containing at least about 6 carbon atoms wherein the metal is selected from the group consisting of transition metals, zinc, mercury, antimony and lead, (B) at least one isothiazolone compound represented by the structural formula

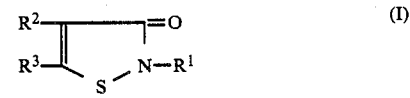

wherein $R^1$ is an alkyl, alkenyl or alkynyl group of 1 to about 18 carbon atoms; a cycloalkyl group having a 3 to 6 carbon atom ring and up to about 12 carbon atoms; an aralkyl or aryl group of up to about 10 carbon atoms; $R^2$ is hydrogen, halogen or a lower alkyl group; and $R^3$ is hydrogen, halogen or a lower alkyl group, and p0 (C) at least one solvent/diluent.

The solvent/diluent may be water or one or more hydrocarbon solvents. The novel compositions of the invention are useful in preserving wood, and when so used, the compositions also may include flame retardants, water repellents, odorants, insecticides, etc.

24 Claims, No Drawings

COMPOSITIONS AND PROCESS FOR PRESERVING WOOD

FIELD OF THE INVENTION

The present invention relates to novel compositions and to a process for preserving wood. More particularly, the compositions comprise certain metal salts and isothiazolones. The invention also relates to wood treated with the compositions of the invention.

In order to prevent decay of wood and timbers, and thereby increase their life, it is common practice to impregnate the wood or timbers with a preservative such as creosote, mixtures of inorganic compounds which are dissolved or dispersed in water, or certain organic compounds which are dissolved in petroleum distillates. The protection afforded by the application of these materials is dependent upon deep and reasonably uniform penetration into the wood or timber by the preservative material.

The subject of wood treatment and wood preservation is discussed in some detail in the two-volume treatise entitled "Wood Deterioration and its Prevention by Preservative Treatments", Darrel D. Nicholas, Editor, Syracuse Wood Science Series 5, Syracuse University Press, Syracuse, N.Y., 1973. Among the examples of wood preservatives described therein are various creosote compositions, pentachloro-phenol, copper naphthenate, copper-8-quinolinolate, organotin compounds, organomercury compounds, zinc naphthenate, chlorinated hydrocarbons, ammoniacal copper arsenite (ACA), acid copper chromate (ACC), zinc salts such as zinc chloride, zinc oxide and zinc sulfate, chromated copper arsenate (CCA), etc.

Wood preservatives such as those described above have been applied to the wood as solutions, emulsions, pastes or dispersions in liquid hydrocarbons and/or aqueous systems. In many applications, the use of aqueous systems is preferred over liquid hydrocarbons because of the odors, flammability and often toxic nature of the liquid hydrocarbons. U.S. Pat. No. 4,507,152 describes aqueous compositions having fungicidal and insecticidal properties which can be used in the treatment of wood. The aqueous compositions comprise oilsoluble metal salts of organic carboxylic axis, halopyridyl phosphates and surfactants. The compositions can be utilized to penetrate wood, and the wood treated with this aqueous system is resistant to fungi and insects.

Wood preservatives which are utilized as aqueous ammoniacal solutions of fatty acid salts are described in U.S. Pat. No. 4,001,400, and aqueous solutions of metal salts of carboxylic acids and ammonia and/or ammonium compounds are described in U.S. Pat. No. 4,193,993. The ammonia and/or ammonium compounds are utilized to maintain the metal salt in solution. British Patent Specification GB No. 2049430 describes water-based fungicidal compositions which comprise a cuprammonium complex of a C1-4 monocarboxylic acid and a C1-4 monocarboxylate of a metal selected from an alkaline earth metal, zinc and manganese. The compositions are useful for treating crops such as vines, coffee, tea, apples, pears, etc., and the compositions may be used as paint biocides as a wood preservatives.

The most common commercial procedure for impregnating wood involves subjecting wood to the preservative under relatively high pressures such as 50–150 pounds to the square inch for a substantial period of time such as from one hour to 24 hours. The process also may require relatively high temperatures such as from about 75° C. to about 105°–110° C.

The use of substituted-isothiazolones as wood preservatives has been studied and reported by D.D. Nicholas et al at the Fifteenth Annual Meeting in Sweden of the International Research Group on Wood Preservation (Document No. IRPG/WP/3306), May 28–June 1, 1984. The authors evaluated the use of 4,5-dichloro-2-n-octyl-4-isothiazolone in wood treatments. The compound was found to be effective against wood decaying brown-rot fungi. A number of 3-isothiazolones are described in U.S. Pat. No. 3,761,488, and these compounds and compositions containing these compounds are reported to exhibit a broad spectrum of biocidal properties. The compounds are reported to be particularly effective for the control of microorganisms.

Metal salt complexes of 3-isothiazolones and compositions containing them are described in U.S. Pat. Nos. 4,396,413 and 4,150,026. The metal of the metal salts may be any one of barium, cadmium, calcium, chromium, cobalt, copper, iron, lead, lithium, magnesium, manganese, mercury, nickel, silver, sodium, strontium, tin or zinc. Acetates, oxalates and maleates are included in a variety of metal salts disclosed.

The above-described prior art represents a small sampling of the suggestions which have been made for treating wood water water and/or preservative materials to prevent decay. In spite of these many suggestions made in the prior art, there continues to be a need for inexpensive, safe, non-toxic, and non-corrosive treatment which is effective is imparting fungicidal insecticidal and other properties to wood and which results in the uniform penetration of the preservatives into the wood.

SUMMARY OF THE INVENTION

Novel compositions of matter and processes for utilizing such compositions in preserving wood are described. More particularly, the novel compositions comprise (A) at least one metal salt of an organic carboxylic acid containing at least about 6 carbon atoms wherein the metal is selected from the group consisting of transition metals, zinc, mercury, antimony and lead, and (B) at least one isothiazolone compound represented by the structural formula

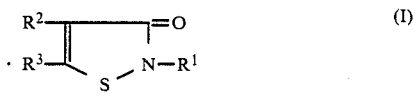 (I)

wherein $R^1$ is an alkyl, alkenyl or aklynyl group of 1 to about 18 carbons atoms; a cycloalkyl group having a 3 to 6 carbon atom ring and up to about 12 carbon atoms; an aralkyl or aryl group of up to about 10 carbon atoms; $R^2$ is hydrogen, halogen or a lower alkyl group; and $R^3$ is hydrogen, halogen or a lower alkyl group.

The novel compositions also may include at least one solvent/diluent which may be water or one or more hydrocarbon solvents, and one or more surfactants. The novel compositions of the invention are useful in preserving wood, and when so used, the compositions also may include flame retardants, water repellents, odorants, insecticides, etc.

DESCRIPTION OF THE PREFERRED EMBODIMENTS

The compositions of the present invention comprise a mixture of certain metal salts and certain isothiazolone compounds.

(A): Metal Salts

The mixtures of the present invention contain a preservative-effective amount of at least one metal salt of an organic carboxylic acid containing at least about 6 carbon atoms wherein the metal is selected from the group consisting of transition metals, zinc, mercury, antimony and lead. When the compositions contain the optional solvent/diluent (i) it is preferred that the metal salt is soluble in the solvent/diluent. The oil-solubility of the metal salts used in the mixture is believed to contribute to the advantageous and desirable results which are obtained. Since the organic compound is oil-soluble and essentially hydrophobic, it therefore does not have a tendency to be extracted or leached from the treated wood even over an extended period of time.

Particularly preferred types of oil-soluble metal salts which are useful in the mixtures of the present invention are the acid, neutral and basic salts of organic carboxylic acids. These salts also are known in the art as "soaps", and the two terms are used interchangeably in this specification and in the claims.

The choice of metal contained in the salts will depend upon the properties which are desired to be imparted to the wood being treated, availability, cost and effectiveness. For example, copper salts such as copper naphthenate are fungicides as well as insecticides. Certain metals are more commonly used in the method of the invention, and these include, copper, zinc, zirconium, chromium, iron, antimony, lead and mercury. Salts containing a mixture of the ions of two or more of these metals also can be used.

As mentioned, the salts can be acid, neutral or basic. The acid salts contain insufficient metal cation to neutralize the acid. The neutral salts contain an amount of metal cation just sufficient to neutralize the acidic groups present in the salt anion. The basic salts contain an excess of metal cation and are often referred to as overbased, hyperbased or superbased salts. These acid, basic and neutral salts preferably are of oil-soluble organic carboxylic acids and mixtures of such acids.

The carboxylic acids from which suitable acid, neutral and basic salts can be prepared include aliphatic, cycloaliphatic and aromatic mono- and polybasic carboxylic acids containing 6 or more carbon atoms. The organic carboxylic acids can be either natural or synthetic or mixtures thereof. The examples of natural acids, although usually refined, include straight and branched chain carboxylic acids and mixtures such as tall oil acids and cyclic carboxylic acids such as naphthenic acids. A variety of synthetic carboxylic acids, and particularly aliphatic carboxylic acids or mixtures thereof is useful.

The metal salts or soaps can be prepared by fusion or precipitation methods. The soaps normally are prepared in an inert liquid medium such as a hydrocarbon oil or solvent. The organic carboxylic acids generally will have at least 6 carbon atoms and as many as 30 carbon atoms, but when more than one carboxylic acid is employed, carboxylic acids containing as few as 2 carbon atoms may be employed as one of the acids of the mixture. Examples of useful organic carboxylic acids include acetic acid, propionic acid, butyric acid, isopentanoic acid, hexoic acid, 2-ethyl butyric acid, nonylic acid, decanoic acid, 2-ethylhexoic acid, isooctanoic acid, isononanoic acid, neodecanoic acid, lauric acid, palmitic acid, stearic acid, oleic acid, linoleic acid, naphthenic acid, and commercially available mixtures of two or more carboxylic acids such as naphthenic, tall oil acids, rosin acids, etc.

Examples of acid salts are acid copper salts containing less than a stoichiometric equivalent of copper per acid equivalent. For metals other than copper, the basic salts or soaps are preferred since these contain higher amounts of metal. For example, solutions of normal zinc salts of monocarboxylic acids such as neodecanoic acid contain about 6% zinc by weight whereas a solution of a basic zinc neodecanoate can contain up to about 16% by weight or more of zinc.

Basic metal salts or soaps of carboxylic acids also can be prepared by methods well known in the arts. Examples of neutral and basic salts and of metal salt complexes as well as their preparation can be found in, for example, U.S. Pat. Nos. 2,251,798; 2,955,949; 3,723,152; and 3,941,606 which disclosures are herein incorporated by reference. Some of the basic salts have been referred to as complexes because they are not simple salts. For example, the basic compositions described in U.S. Pat. No. 3,941,606 are referred to as "metal carboxylate-alkoxy alcoholate" complexes. For the purpose of this invention such basic complexes are to be included in the term metal salts or soaps as used in this specification and claims.

Specific examples of the salts or soaps which are useful in the invention include those described below in Table I and the following specific examples.

TABLE I

| Carboxylate Metal Salts | | | |
| --- | --- | --- | --- |
| Component | Metal | Metal Content (Wt. %) | Acid |
| A-1-1 | Cu | 16 | neodecanoic |
| A-1-2 | Cu | 11 | neodecanoic |
| A-1-3 | Cu | 10 | naphthenic |
| A-1-4 | Zn | 18 | 2-ethyl hexoic |
| A-1-5 | Zn | 8 | naphthenic |
| A-1-6 | Zn | 10 | mixture of $C_{9-13}$ |
| A-1-7 | Pb | 10 | naphthenic |

The preparation of the above-described metal salts is illustrated by the following examples. All parts and percentages in the following examples, and elsewhere in the specification and claims, are by weight unless otherwise stated.

Example A-1-1

A mixture of 260 parts of crude neodecanoic acid, 103 parts of propionic acid, 400 parts of mineral spirits, 172 parts of copper powder, 91 parts of Methyl Cellosolve, 14 parts of dipropylene glycol, 70 part of water, 10 parts of octyl-phenoxy polyethoxy ethanol (Triton X-15 from Rohm & Haas Company) and 3 parts of Santoflex-77 is prepared and sparged with air while heating to a temperature of about 80° C. Reaction under these conditions continues for about 6 hours. A small amount of boric acid (7 parts) is added and the heating is continued at 80° C. with air sparging. The reaction is continued at this temperature until about 1.8 equivalents of metal are reacted per equivalent of acid (total, 14 hours). The mixture is heated for an additional 2 hours at a temperature of about 150° C. until about 1.9 equivalents of metal are reacted per equivalent of acid. The air blowing is terminated, and an inert nitrogen atmosphere is employed while the mixture is slowly heated to about 150° C. over a period of 8 hours while excess water is removed.

Four approximately equal proportions of amyl phosphate totalling 176 parts are added at 3-hour intervals while maintaining a temperature of about 145° C. and a nitrogen atmosphere. The mixture then is cooled to about 125° C., settled to remove excess copper and filtered.

The filtered product is heated under vacuum to a temperature of about 150° C. in order to remove the mineral spirits to yield the desired concentration of metal.

The compositions of Examples A-1-2 through A-1-7 in Table I can be prepared by methods similar to those described above for A-1-1 or by alternative procedures known in the art.

Example A-1-8

A mixture of 840 parts of distilled naphthenic acid, 176 parts of 2-ethyl hexanoic acid, 512 parts of mineral spirits, 48 parts of Carbitol (a diethylene glycol ether available commercially from Union Carbide Corp.), 4.8 parts of acetic acid, 1.6 parts of water and 10.9 parts of an anti-foam agent is charged to a reactor, and the mixture is heated with agitation to a temperature of about 65° C. The mixture is sparged with carbon dioxide and 214.4 parts of zinc oxide are added to the mixture which is then heated to a temperature of about 105° C. The reaction is continued at this temperature while periodic checks are made for percent zinc, the acid value and percent water. If necessary, the acid value is adjusted to minus 33 to minus 38 for 10% zinc. If the water content is over 0.4%, the mixture is dehydrated.

About 100 parts of filter aid are added with stirring to the mixture which is then filtered. The filtrate is a clear liquid which is adjusted to a zinc content of 10% using mineral spirits to form the desired product.

Mineral spirit solutions of metal carboxylate salts of the type described above are available commercially such as from Mooney Chemicals, Inc., Cleveland Ohio, 44113, under the general trade designations TENCEM, CEM-ALL, NAP-ALL, HEX-CEM, LIN-ALL, and NEO-NAP. These mineral spirit solutions can be used in preparing the penetrating solutions of the present invention or can be adopted for use by mixing said mineral spirit solutions with other hydrocarbon solvents, or alternatively, the mineral spirits may be removed and the residue mixed with other hydrocarbon solvents, e.g., higher boiling solvents.

Water-dispersible solutions/dispersions of metal salts also are available from Mooney Chemicals, Inc. under the general trade designation M-GARD ™. The metal content of these salts also ranges from about 4% to about 10%, but these solutions/dispersions already contain the desired surfactants and can be readily mixed with isothiazolone compounds and water to form the desired aqueous systems.

Mixtures of the carboxylic acid salts such as those described in Table I are easily prepared and utilized in accordance with the invention. For example, a mixture in accordance with the invention is prepared from equal parts of components A-1-1 and A-1-6 resulting in a mixture containing 8% copper and 5% zinc. A mixture of two parts of component A-1-1 with one part of component A-1-6 will contain 10.7% copper and 3.3% of zinc.

The metal salts which are utilized in the solutions of the present invention also may be prepared by conventional procedures such as by the reaction of copper metal or a copper salt with the acid, for example, naphthenic acid. When the acid is a liquid, solvents are not generally required. The metal salts prepared in this manner may be either acid or neutral salts as described above and can be dissolved in hydrocarbon solvents for use in the process of the present invention.

Examples of other neutral and basic salts include lead naphthenate, lead neodecanoate, lead 2-ethyl hexoate, lead tallate, zinc tallate, chromium 2-ethyl hexoate, chromium tallate, chromium oleate, antimony octoate, antimony oleate, iron naphthenate, iron tallate, phenyl mercury oleate, mercury dioleate, etc.

Although a wide variety of metal salts can be utilized in the process of the present invention, it generally is preferred that the metal salt utilized in the process is a fungicide, and, accordingly, the metal of the metal salt generally will be at least one of zinc, copper, chromium, zirconium, iron, antimony, lead or mercury. In addition to the metal salts described above, other metal salts known in the art can be applied to wood in accordance with the process of the present invention. For example, metal salt compositions are described in U.S. Pat. No. 4,374,854 which are mixtures of salts of primary and/or secondary saturated acyclic carboxylic acids and a tertiary saturated acyclic carboxylic acid with zinc or copper. Such salts are useful in the compositions of the present invention.

(B): The Isothiazolone Compounds

In addition to the above-described transistion metal salts, the novel compositions of the present invention also contain at least one isothiazolone compound represented by the structural formula

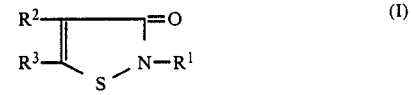

where $R^1$ is an alkyl, alkenyl or alkynyl group of 1 to about 18 carbon atoms; a cycloalkyl group having a 3 to 6 carbon atom ring and up to about 12 carbon atoms; an aralkyl or aryl group of up to about 10 carbon atoms; $R^2$ is hydrogen, halogen or a lower alkyl group; and $R^3$ is hydrogen, halogen or a lower alkyl group.

The alkyl, alkenyl, alkynyl, cycloalkyl, aralkyl, and aryl groups may be substituted or unsubstituted.

By a substituted alkyl group is meant an alkyl group having one or more of its hydrogen atoms replaced by another substituent group. Examples of the substituted alkyl groups which characterize 3-isothiazolones useful in this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, alkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituted aralkyl groups which characterize 3-isothiazoles useful in this invention include halogen-, lower alkyl-, or lower alkoxy-substituted aralkyl groups, and the like.

By a substituted aryl group is meant an aryl group, such as benzene, naphthalene, or pyridine, having one or more of the hydrogen atoms on the aryl ring replaced by another substituent group. Examples of such substituent groups include halogen, nitro, lower alkyl, lower alkyl-acylamino, lower carbalkoxy, sulfamyl, and the like.

Representative $R^1$ substituents include methyl, ethyl, propyl, isopropyl, n-butyl, t-butyl, hexyl, octyl, decyl, pentadecyl, octadecyl, cyclopropyl, cyclohexyl, benzyl, 3,4-dichlorobenzyl, 4-methoxybenzyl, 4-chlorobenzyl, 3,4-dichlorophenyl, hydroxymethyl, chloromethyl, chloropropyl, diethylaminoethyl, cyanoethyl, carbomethoxyethyl, ethoxyethyl, 2-methoxy-1bromoethyl, 3,3,5-trimethylcyclohexyl, phenoxyethyl, p-chloroanilinomethyl, phenylcarbamoxymethyl, allyl, propynyl, vinyl, carboxyethyl, 1-isothiazolonylethyl, and 1,2,2,-trichlorovinyl, Preferably $R^1$ contains from about 4 to about 18 carbon atoms.

Representative $R^2$ substituents include hydrogen, bromo, chloro, iodo, methyl, ethyl, propyl, isopropyl, butyl, and t-butyl.

Representative $R^3$ substituents are hydrogen, chloro, bromo, iodo, methyl, ethyl, propyl, isopropyl, butyl, t-butyl, chloromethyl, chloropropyl, bromomethyl, bromoethyl, and bromopropyl.

Specific examples of typical isothiazolone compounds (I) useful in this invention as component (B) include the compounds in Table II.

TABLE II

| Example | $R^1$ | $R^2$ | $R^3$ | Name- (-3-isothiazolone) |
|---|---|---|---|---|
| 1 | $nC_3H_7$ | H | H | 2-n-propyl- |
| 2 | n-butyl | H | H | 2-n-butyl- |
| 3 | t-butyl | H | H | 2-t-butyl- |
| 4 | $C_6H_{11}$— | H | H | 2-cyclohexyl- |
| 5 | $n-C_8H_{17}$— | H | H | 2-n-octyl- |
| 6 | $C_6H_4CH_2$— | H | H | 2-benzyl- |
| 7 | $CH_3$ | H | Cl | 5-chloro-2-methyl- |
| 8 | $C_6H_4CH_2$— | H | Cl | 5-chloro-2-benzyl- |
| 9 | $CH_3$ | Br | Cl | 4-bromo-5-chloro-2-methyl- |
| 10 | $HOCH_2$ | H | H | 2-hydroxymethyl- |
| 11 | $nC_{12}H_{25}$ | H | H | 2-n-dodecyl- |
| 12 | $t-C_8H_{17}$— | Cl | H | 4-chloro-2-t-octyl- |
| 13 | $nC_8H_{17}$ | H | Cl | 2-n-octyl-5-chloro- |
| 14 | $NCCH_2CH_2$— | H | H | 2-(2-cyanoethyl)- |
| 15 | $HC\equiv C-CH_2$— | H | H | 2-propynyl- |
| 16 | $CH_2=CH$— | H | H | 2-vinyl- |
| 17 | $CH_2=CH$— | H | Cl | 5-chloro-2-vinyl- |
| 18 | $CH_3OCH_2$— | H | H | 2-methoxymethyl- |
| 19 | $ClCH_2CH_2$ | H | H | 2-(2-chloroethyl)- |
| 20 | $C_6H_5$— | H | H | 2-phenyl- |
| 21 | $t-C_8H_{17}$— | Cl | Cl | 4,5-dichloro-2-t-octyl- |
| 22 | $i-C_3H_7$ | $CH_3$ | H | 4-methyl-2-isopropyl- |
| 23 | $CH_3$— | $CH_3$ | H | 2,4-dimethyl- |
| 24 | $CH_3$ | Cl | Cl | 4,5-dichloro-2-methyl- |
| 25 | $n-C_8H_{17}$— | Cl | Cl | 4,5-dichloro-2-n-octyl- |

The isothiazolone compounds useful as component (B) in the compositions of the present invention may be prepared by methods known in the art. For example, all of the isothiazolones with the exception of the hydroxyalkyl, alkenyl and alkynyl derivatives, can be prepared by the cyclization of a substituted disulfide-amide having the formula

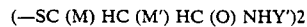

(—SC (M) HC (M') HC (O) NHY')2 wherein M and M' are hydrogen or lower alkyl and Y' can be any of the groups identified by $R^1$ in Formula I as defined above except alkenyl, alkynyl and lower hydroxy alkyl groups. The cyclization is accomplished by reacting the disulfide-amide with a halogenating agent. Any halogenating may be employed in this reaction, and typical halogenating agents include chlorine, bromine, sulfuryl chloride, sulfuryl bromide, N-chlorosuccinimide, iodine monochloride, etc. Bromine and chlorine are preferred halogenating agents. The cyclization takes place when 3 mole equivalents of the halogenating agent are employed in the reaction. By providing an excess of halogenating agent, the isothiazolone may be halogenated in the 4- and/or 5-positions. When 5 mole equivalents of the halogenating agent are utilized in the reaction, mono-halogenation can take place. For dihalogenation to occur, 7 mole equivalents of the halogenating agent are required. The preparation of isothiazolones having the 4- and 5-positions substituted with different halogens is accomplished by the halogenation of an isothiazolone already halogenated in one of the two positions. For example, if a 4-bromo-5-chloro3-isothiazolone is desired, it can be obtained by brominating the 5-chloro, 3-isothiazolone or by chlorinating the 4-bromo derivative.

The cyclization process will proceed over a wide temperature range, and temperature is not critical to the reaction. Generally, the cyclization will be carried out in the range of 0° to 100° C. The reaction is carried out in an inert, non-aqueous solvent, such as, for example, benzene, toluene, xylene, ethyl acetate or ethylene dichloride. Other procedures for preparing various substituted isothiazolones useful as component (B) in the compositions of the present invention are described in U.S. Pat. No. 3,761,488, and the disclosure of this patent relating to various isothiazolone compounds useful in the present invention and the preparation of such isothiazolone compounds hereby is incorporated by reference.

The following examples are presented to illustrate procedures for preparing some of the 3-isothiazolone compounds of Table II useful as component (B) in the present invention. Further examples of the preparation of various isothiazolone compounds are found in the above-identified U.S. Pat. No. 3,761,488.

Example 7

Preparation of 5-chloro-2-methyl-3-isothiazolone

To an ethylene dichloride (1 liter) slurry of dithio-N,N'-dimethyldipropionamide, 70.9 g. (0.3 mole), there are added at 10°–15° C. over 1.5 hours, 121.5 g. (0.9 mole) of sulfuryl chloride. After addition, the reaction slurry is allowed to warm to 20°–25° C. and stirred overnight to assure completion of the reaction. The slurry is then filtered to give 37.1 g. of 2-methyl-3-isothiazolone hydrochloride. The ethylenedichloride filtrate, upon evaporation to approximately one-half volume, yielded an additional quantity (30.5 g.) of less pure hydrochloride. Complete evaporation of the ethylene dichloride filtrate gives 24.7 g. of oily residue which upon sublimation at 0.1 mm. (40°–60° C.) yields 11.5 g. of 5-chloro-2-methyl-3-isothiazolone, m.p. 44°–47° C.

Example 10

Preparation of 2-hydroxymethyl-3-isothiazolone

Aqueous formaldehyde (37%), 4.5 g. (0.056 mole) is diluted with 25 ml. of water, and then 3.8 g. (0.028 mole) of potassium carbonate are added. Thereafter, 5.5 g. (0.055 mole) of 3-hydroxyisothiazole are added to the formaldehyde solution in one portion. A solid precipitate soon forms, and after 2 hours stirring, is filtered off to yield 1.8 g. of white solid 2-hydroxymethyl-3-isothiazolone.

Example 12

Preparation of 4-chloro-2-t-octyl-3-isothiazolone

To a solution of 10.7 g. (0.05 mole) of 2-t-octyl-3-isothiazolone in 100 ml. of chloroform is added in a single portion 13.3 g. (0.1 mole) of N-chlorosuccinimide. The mixture warms somewhat but does not require cooling. After stirring for 2.5 hours, the mixture is filtered giving 7.5 g. of crude succinimide. The filtrate is evaporated under reduced pressure and the residue dissolved in ether. The ether solution is extracted with water, dried over anhydrous magnesium sulfate, and evaporated to a mixture of solid and oil. The oil is washed from the solid with hexane leaving 1.7 g. (14%) of white 4-chloro-2-t-octyl-3-isothiazolone, m.p. 137°-140°.

Example 16

Preparation of 2-vinyl-3-isothiazolone

In 300 ml. of vinyl acetate there are dissolved 5.0 g. of mercuric acetate by gentle refluxing. The solution is then cooled to 0° C. and 0.4 ml. of 30% fuming sulfuric acid is added, followed by 20 g. (0.20 mole) of 3-hydroxyisothiazole. During five days the solution is heated at 50° C. The solution is then cooled and 4.5 g. of sodium acetate are added. After stirring for 3 hours, the mixture is filtered, and the excess vinyl acetate is removed under vacuum. Distillation of the residue yields 11.3 g. (45%) of 2-vinyl-3-isothiazolone, b.p. 90-94 (0.05 mm.). The distilled product solidifies and after crystallization from ether, hexane has an m.p. 56°-58° C.

Example 24

Preparation of 4,5-dichloro-2-methyl-3-isothiazolone

To a solution of 5.2 g. (0.045 mole) of 2-methyl-3-isothiazolone in 100 ml. of ethyl acetate at -70° C. is added 6.08 g. (0.045 mole) sulfuryl chloride over 45 minutes. The reaction is stirred at this temperature for 4 hours and then is allowed to come to room temperature. The ethyl acetate is removed by evaporation from the resulting slurry, and the solid thus obtained is extracted with benzene. Filtration and evaporation of the benzene yields 4 g. (96% based upon sulfuryl chloride of 4,5-dichloro-2-methyl-3-isothiazolone, which is crystallized from ligroin (90°-120° C.), m.p. 114°-117° C.

A number of isothiazolone compounds useful as component (B) in the present invention are available commercially from, for example, the Rohm & Haas Company, Philadelphia, Pa. under various trade names. For example, 2-n-octyl-3-isothiazolone is available under the general trade name Skane M-8. The corresponding 4,5-dichloro-n-octyl-derivative is available under the trade designation Kathon 287. The product 5-chloro-2-methyl-3-isothiazolone is available under the general trade designation Kathon 886. Also available commercially from Rohm & Haas is a mixture of 5-chloro-2-methyl-3-isothiazolone and 2-methyl-3-isothiazolone.

The compositions of the present invention which comprise mixtures of metal salts (A) and isothiazolone compounds (B) may contain these two components in varying amounts, and generally, the weight ratio of metal in (A) to isothiazolone compound (B) contained in the composition is from about 0.1:1 to about 50:1. The specific ratio of (A):(B) may be varied by one skilled in the art depending on the intended use of the composition and the specific properties desired. In a preferred embodiment, the weight ratio of (A) to (B) in the compositions of the present invention is from about 0.2:1 to about 25:1.

In one embodiment of the present invention, the compositions of the present invention also may contain (C) at least one solvent/diluent. The amount of solvent/diluent included in the compositions of the present invention also may vary over a wide range depending on the desired concentration of components (A) and (B). Thus, if concentrates are desired, then the amount of solvent/diluent is kept to a minimum, the concentration of components (A) and (B) is higher. When the compositions of the present invention are to be used in preserving wood, more dilute mixtures are preferred and the amount of solvent/diluent incorporated into the composition is increased accordingly. The amount of solvent/dilulent included in the compositions of the invention can be utilized to vary the amount of metal and/or isothiazolone compound contained in the diluted compositions. The compositions of the present invention which comprise a mixture of components (A), (B) and (C) generally may contain from about 0.001 to about 10% by weight of metal and from about 0.01 to about 5% by weight of the isothiazolone compound (B) based on the total weight of the composition. The remainder of the composition will be the solvent/diluent and any other optional additives as described more fully hereinafter. Generally, when aqueous systems are prepared, the system may contain some hydrocarbon solvent but less than about 30% by weight of the hydrocarbon solvent.

(C): The Solvent/Diluent

The third component included in the compositions of the present invention is at least one solvent/diluent. The solvent/diluent may be water or a liquid hydrocarbon. When components (A) and (B) are soluble in the solvent/diluent, the composition generally is a solution, and when either or both of components (A) and (B) are insoluble in he solvent/diluent, the compositions of the invention may be dispersions, emulsions or micro-emulsions.

In one embodiment, component (C) is a liquid hydrocarbon in which either or both of components (A) and (B) are soluble, and preferably, both components (A) and (B) are soluble in the liquid hydrocarbon.

Suitable hydrocarbon liquids include aromatic and aliphatic hydrocarbon solvents such as petroleum hydrocarbon solvents, aromatic hydrocarbons, aromatized petroleum distillates, and mixtures of petroleum hydrocarbon solvents and aromatic hydrocarbons. Halogenated hydrocargon solvents are included within the term "hydrocarbon solvents" as utilized in this application and claims. Examples of useful solvents include xylene, toluene, naphtha, light mineral oil, etc.

Examples of specific hydrocarbon solvents useful in the present invention include solvents which are principally aliphatic such as No. 2 diesel fuel, Pennzoil 510 oil and 140 Mineral spirits, and solvents which are principally aromatic such as Shell P9 oil (Shell Chemical Co.) and Lilyblad Base L Oil.

(D): Surfactant

The compositions of the invention also may, and generally do, contain (D) at least one surfactant. The surfactants may be incorporated into the compositions of the invention by first preparing concentrates of the surfactant with either or both of components (A) and (B) which are then diluted with the solvent/diluent (C), or the surfactant can be incorporated into the compositions of the invention after the concentrates comprising (A), (B) and (C) have been diluted.

Preferably, the surfactants are anionic or nonionic surfactants. Many such surfactants are known in the art. See, for example, McCutcheon's "Detergents and Emulsifiers", 1979, North American Edition, published by McCutcheon's Division, MC Publishing Corporation, Gen Glen Rock, N.J., U.S.A., particularly pages 15-20 which are hereby incorporated by reference for their disclosure in this regard.

In general, the nonionic surfactants such as those containing ether linkages are particularly useful. Examples of such ether-containing surfactants are those having the general formula $$R_1-O-[(CH_2)_nO]_xH$$

wherein R1 is an aryl or alkyl group containing from about 6 to about 20 carbon atoms, n is 2 or 3, and x is an integer between 2 and 100. Such surfactants are produced generally by treating fatty alcohols or alkyl-substituted phenols with excess ethylene oxide or propylene oxide. The alkyl carbon chain may contain from about 14 to about 24 carbon atoms and may be derived from a long chain fatty alcohol such as oleyl alcohol or stearyl alcohol.

Nonionic polyoxyethylene compounds of this type are described in U.S. Pat. No. 3,855,085. Such polyoxyethylene compounds are available commercially under the general trade designations "Surfynol" by Air Products and Chemicals, Inc. of Allentown, Pa., and under the designation "Pluronic" or "Tetronic" by BASF Wyandotte Corp. of Wyandotte, Mich. Examples of specific polyoxyethylene condensation products include "Surfynol 465" which is a product obtained by reacting about 10 moles of ethylene oxide with 1 mole of tetramethyldecynediol. "Surfynol 485" is the product obtained by reacting 30 moles of ethylene oxide with tetramethyldecynediol. "Pluronic L 35" is a product obtained by reacting 22 moles of ethylene oxide with polypropylene glycol obtained by the condensation of 16 moles of propylene oxide. Also useful is Atlox 1045A from ICI America, Inc. Which is a polyoxyalkylene sorbitol oleate-laurate mixture.

Amine, long chain fatty amine, long chain fatty acid, alkanol amines, diamines, amides, alkanol amides and polyglycol-type surfactants known in the art are also useful. One type found particularly useful is the group obtained by the addition of a mixture of propylene oxide and ethylene oxide to diamines. More specifically, compounds formed by the addition of propylene oxide to ethylene diamine followed by the addition of ethylene oxide are useful and are available commercially from BASF Wyandotte Inc. Chemical Group under the general trade designation "Tetronic".

Carbowax-type wetting agents which are polyethylene glycols having different molecular weights have been found to give good results. For example Carbowax No. 1000 has a molecular weight range of from about 950 to 1050 and contains from 20 to 24 ethoxy units per molecule. Carbowax No. 4000 has a molecular weight range of from about 3000 to 3700 and contains from 68 to 85 ethoxy units per molecule. Other known nonionic glycol derivatives such as polyalkylene glycol ethers and methoxy polyethylene glycols which are available commercially can be utilized as surfactants in the compositions of the invention.

Anionic surfactants also are useful in the aqueous systems of the invention. Among the useful anionic surfactants are the widely-known metal carboxylate soaps, organo sulfates, sulfonates, sulfocarboxylic acids and their salts, and phosphates. Various anionic surfactants are readily available commercially, and further information about anionic surfactants can be found in the test "Anionic Surfactants" Parts II and III, edited by W. M. Linfield, published by Marcel Dekker, Inc., N.Y., 1976. Examples of anionic surfactants available from ICI America, Inc. include Atlas G-2205 which is an aromatic phosphate and Atlas G-3300 which is an alkyl aryl sulfonate. Examples of anionic surfactants available from Rohm & Haas Company include Triton 770 which is a dioctyl sodium sulfosuccinate, Triton H-55 which is a phosphate surfactant, potassium salt, Triton W-30 and Triton X200 which are sodium salts of alkyl aryl polyether sulfonates, etc.

Mixtures of the nonionic and anionic surfactants can and are generally utilized in the aqueous systems of the present invention. The amount of surfactant contained in the compositions can vary over a wide range, but is generally from 0.10% to about 20% and more preferably between 0.10% and 15%.

The aqueous systems of the present invention can be prepared by mixing the metal salt, isothiazolone compound, and the surfactants with sufficient water to provide the desired levels of ingredients. Alternatively, and more preferably, the aqueous systems are prepared from water-dispersible additive concentrates which contain the desired metal salt, isothiazolone compound, one or more surfactants and a hydrocarbon solvent. As mentioned above, such additive concentrates are available commercially such as from Mooney Chemicals, Inc. under the general trade designation M-GARD ™. Moreover, such water-dispersible additive concentrates can be prepared from commercially available solutions of metal salts and mineral spirits and by blending the mineral spirit solutions with the desired surfactants with or without additional hydrocarbon solvents such as mineral oils. For example, a water-dispersible additive concentrate can be prepared from the metal salt solutions in mineral spirits illustrated above as Examples B-1 to B-7 by thoroughly mixing the mineral spirit solutions with mineral oil and surfactants. A specific example of such a procedure is the blending of 800 parts of the product of Example B-7 with 100 parts of mineral oil, 20 parts of Atlas G-3300 and 100 parts of Atlas G-1096. Similar water-dispersible additive concentrates can be prepared from compositions identified as B-1 to B-7 utilizing the same or other surfactants.

The water-dispersible additive concentrates of the types described above can be converted to the aqueous systems utilized in the invention by dilution with water. This dilution usually is accomplished by standard mixing techniques. This offers a convenient procedure since the additive concentrate can be shipped to the point of use before the water is added, thereby reducing the cost of shipping.

The above mixtures of components (A), (B) and (C) can be prepared by techniques known in the art such as by dissolving solid metal salts and isothiazolone compound in the hydrocarbon solvent or mixture of hydrocarbon solvents. Alternatively, when the metal salt is available in concentrated solution form, the concentrate can be diluted with a hydrocarbon solvent and the isothiazolone compound added to form the treating or penetrating solution containing the desired amount of metal salt and isothiazolone. The order of mixing the three components is not critical.

The compositions used in the method of the present invention also may contain other additives depending on the intended use for the composition. When the compositions of the invention are to be used in preserving wood, other additives can be included which impart desirable properties to the treated wood. For example, the compositions may contain anti-foam agents, surfactants, antioxidants, flame retardant compositions coloring agents, insecticides, odorants, moldicides, wood stabilizing agents, etc. The amount of such optional additives included in the compositions of the invention may vary over a rather wide range although amounts of from about 0.01 to about 5% of these compositions generally are satisfactory.

Inorganic fire retardant compositions are particularly useful in the compositions of the invention. Examples of inorganic materials include metal oxides which are well known in the art such as antimony oxide, etc. Examples of organic fire retardants include a number of halogenated and organophosphorus compounds which may be dispersed in the solutions.

Although the wood which can be treated in accordance with the method of the invention may have a satisfactory appearance for most purposes, the appearance can be modified if desired by imparting different color effects. The present invention contemplates the inclusion of coloring agents in the compositions of the invention. Any of the known oil-soluble or water-dispersible coloring agents can be used. These agents are mixed either with the concentrates of metal salts and isothiazolone compounds described above, or the solutions, and when the wood is immersed in the solutions containing coloring agents, the coloring agents penetrate the wood with the metal salts and isothiazolone and give desirable coloring effects which in many instances emphasize the grain of the wood. Examples of coloring agents which may be used depending on the desired results include: Bruco Creosote Brown RGY available from Bruce Chemical Co., Iron Cem-All available from Mooney Chemical, Inc., and Pylaklor Red Brown LX-6249 available from Pylam Dye Co.

Insecticides also can be included in the compositions of the invention, and it is preferable that the insecticide either be soluble in oil or water. Examples of such insecticides include Drusban TC available from Dow Chemical Ficam 76WP available from BFC Chemicals, Inc. and permethrin available from Mooney Chemicals under the trade designation M-GARD W320 TM.

Odorants can be included in the composition of the invention, and one preferred odorant is point oil. Other compounds having desire odors can be included in the solutions.

Wood-stabilizing agents may be included in he compositions of the invention, particularly when (C) is water, to provide the wood with improved dimensional stability. Such agents remain in the cell walls when the wood is dried, and this bulking action prevents the wood from shrinking. Various chemicals have been suggested for this purpose in the art of wood treating. A useful group of stabilizing agents are the polyalkylene glycols, and more particularly, the polyethylene glycols. The molecular weight of the glycols should be selected so that the glycols are soluble in water. Thus, polyethylene glycols having molecular weight of up to about 6000 are desirable because these generally are water-soluble. Various of these polyethylene glycols are available commercially.

The method of the present invention for preserving wood comprises contacting the wood with the compositions of the invention comprising components (A), (B) and (C) and, optionally (D) as described above for a period of time sufficient to enable the desired amount of transition metal salt and isothiazolone compound to penetrate into the wood to a depth which is sufficient to provide the wood with the desired preservative properties. The contact between the wood and the mixtures of the present invention can be effected by brushing, spraying, painting, immersing, etc. Preferably, contact between the wood and the mixtures of the present invention is effected by immersing the wood in the mixture for a period of time which is sufficient to obtain the desired result.

In one method of the present invention, the aqueous system in which the wood is immersed can be maintained at a temperature of from about 5° to about 95° C. at atmospheric pressure. However, the method of the invention can be carried out at ambient temperature thereby eliminating the need for any equipment or materials for heating or cooling the aqueous systems. In some instances, it may be advantageous to heat the aqueous systems to elevated temperatures to increase the rate of penetration.

The method of the invention also can be conducted on wood contained in an enclosed vessel under vacuum or pressure conditions or a combination thereof. The use of pressure for improving the penetration of various chemicals into all types of wood is well known in the art. In this technique, the wood is placed in a chamber which is sealed and evacuated in a regulated cycle which is related to and determined from a consideration of the species of wood. Generally, the period of evacuation will vary from about 15 minutes to one hour, and the pressure within the sealed chamber is brought to a level of about two inches of mercury or less. The purpose of the this step is to remove air and wood volatiles from the wood. The mixtures of the present invention the are introduced into the enclosed container, and the amount of the mixture should be sufficient to immerse the wood completely. The temperature of the mixture is adjusted to at least about ambient temperature and preferably to about 75°–250° F. The pressures utilized in the pressure method can be as high as 250 psig., and are generally from about 50 to 150 psig. Pressurization of the vessel then is initiated, and the pressure is maintained at a desired level for a given period of time. Initially, the pressure within the vessel may decrease as the mixture within the container penetrates into the wood. The pressure may be raised to maintain a desirable level throughout the penetration period of treatment. Stabilization of the pressure within the vessel is an indication that there is no longer any penetration of the liquid into the wood. At this point, the pressure can be released, the vessel drained, and the wood removed. The details of the pressure process, including pressure ranges, concentration of the treating mixture and the cycling of vacuum and pressure can be readily determined by one skilled in the art.

The compositions of the invention can be used for preserving a wide variety of wood types. The actual time of contact of the wood with the solutions will vary depending on a variety of factors such as, for example, (1) the level of pressure within the vessel, (2) the amount of metal salt and isothiazolone compound to be introduced into the wood, (3) the difficulty of penetration into the particular type of wood being treated, and (4) whether the wood is partially seasoned or dry wood. Any type of wood, dry or partially seasoned, can be treated with the compositions of the invention. Examples of wood species which can be treated with the compositions of the invention include Southern Yellow Pine, Western Red Cedar, Douglas fir, Inland fir, Spruce, Hemlock, Sugar Maple, Ash, Walnut, Cherry, White Pine, Red Pine, Birch, Red Oak, White Oak, Elm, Hickory, Linden, Beech, Sycamore, etc.

The following are specific examples of the compositions of the invention. Unless otherwise indicated in the examples, in the specification or in the appended claims, all parts and percentages are by weight and all temperatures are in degrees centigrade.

|  | Amount (%) |
|---|---|
| Example A |  |
| Copper Naphthenate | 8 (as Cu) |
| 4,5-dichloro-2-n-octyl-3-isothiazolone | 2 |
| Atlas G 1096 | 10 |
| Atlas G 3300 | 2 |
| Mineral spirits | remainder |
| Example B |  |
| Zinc Naphthenate | 8 (as Zn) |
| 2-n-octyl-3-isothiazolone | 0.4 |
| Atlas G 1096 | 10 |
| Atlas G 3300 | 2 |
| Mineral spirits | remainder |
| Example C |  |
| Zinc Naphthenate | 0.4 (as Zn) |
| 2-n-octyl-3-isothiazolone | 2 |
| Atlas G 1096 | 10 |
| Atlas G 3300 | 2 |
| Mineral spirits | remainder |
| Example D |  |
| Zinc naphthenate | 8 (as Zn) |
| 2-n-octyl-3-isothiazolone | 2 |
| Atlas G 1096 | 9 |
| Atlas G 3300 | 3 |
| Mineral spirits | remainder |
| Example E |  |
| Composition of Example B | 25 |
| Water | 75 |
| Example F |  |
| Composition of Example D | 2 |
| Water | 100 |
| Example G |  |
| Composition of Example C | 2 |
| Water | 100 |

Wood treated with the preservative compositions of this invention is characterized by improved fungus and mold-resistance. The decay-resistance is greater than when the metal salt or isothiazolone compound is used alone.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A novel composition comprising
   (A) at least one metal salt of an organic carboxylic acid containing at least about 6 carbon atoms wherein the metal is selected from the group consisting of transition metals, zinc, mercury, antimony and lead,
   (B) at least one isothiazolone compound represented by the structural formula

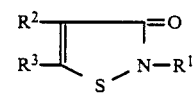 (I)

wherein $R^1$ is an alkyl, alkenyl or alkynyl group of 1 to about 18 carbon atoms; a cycloalkyl group having a 3 to 6 carbon atom ring and up to about 12 carbon atoms; an aralkyl or aryl group of up to about 10 carbon atoms; $R^2$ is hydrogen, halogen or a lower alkyl group; and $R^3$ is hydrogen, halogen or a lower alkyl group, and
   (C) at least one solvent/diluent.

2. The composition of claim 1 wherein the metal is zinc, copper, chromium, iron zirconium, mercury, antimony, lead, or a mixture thereof.

3. The composition of claim 1 wherein the organic carboxylic acid is at least one aliphatic or alicyclic monocarboxylic acid containing from about 6 to about 30 carbon atoms.

4. The composition of claim 1 wherein $R^1$ is an alkyl group containing from 1 to about 18 carbon atoms, and $R^2$ and $R^3$ are hydrogen or halogen.

5. The composition of claim 4 wherein the halogen is chlorine.

6. The composition of claim 1 wherein the weight ratio of metal in (A) to isothiazolone compound (B) is from about 0.1:1 to about 50:1.

7. The composition of claim 1 wherein the solvent/diluent is water or a hydrocarbon solvent.

8. The composition of claim 1 also containing
   (D) at least one surfactant.

9. The composition of claim 8 wherein the surfactant is an anionic or nonionic surfactant or a mixture thereof.

10. The composition of claim 1 also containing effective amounts of at least one odorant, insecticide, flame-retardant, or a mixture thereof.

11. A novel composition useful for preserving wood comprising
    (A) at least one metal salt of an aliphatic or alicyclic monocarboxylic acid containing from about 6 to about 30 carbons atoms wherein the metal is selected from the group consisting of transition metals, zinc, mercury, antimony and lead,
    (B) at least one isothiazolone compound represented by the structural formula

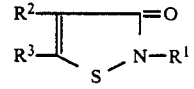 (I)

wherein $R^1$ is an alkyl, alkenyl or alkynyl group of 1 to about 18 carbon atoms; a cycloalkyl group having a 3 to 6 carbon atom ring and up to about 12 carbons atoms; an aralkyl or aryl group of up to about 10 carbon atoms; $R^2$ is hydrogen, halogen or a lower alkyl group; and $R^3$ is hydrogen, or a lower alkyl group;
    (C) water and/or a hydrocarbon solvent, and
    (D) at least one surfactant.

12. The composition of claim 11 wherein the metal of the metal salt is at least one of zinc, copper, chromium, zirconium, iron, antimony, lead or mercury.

13. The composition of claim 12 wherein the metal is zinc or copper or a mixture thereof.

14. The composition of claim 11 wherein $R^2$ in Formula I is an alkyl group containing from about 4 to about 18 carbon atoms, and the halogen, if present, is chlorine or bromine.

15. The composition of claim 11 wherein the weight ratio of metal salt (A) to isothiazolone compound (B) is from about 0.1:1 to about 50:1.

16. The composition of claim 11 wherein the metal content of the composition is from about 0.001 to about 10% by weight.

17. The composition of claim 11 wherein the isothiazolone compound is present in an amount of from about 0.01 to about 5% by weight based on the total weight of the composition.

18. The composition of claim 11 wherein the metal salt (A) is a fungicide.

19. The composition of claim 11 also containing effective amounts of at least one odorant, insecticide, flame-retardant, or mixtures thereof.

20. A composition useful for preserving wood comprising (A) from about 0.001 to about 10% by weight of a metal salt of an organic carboxylic acid wherein the metal is zinc, copper, chromium, iron, antimony, zirconium, lead or mercury, (B) from about 0.01 to about 5% of at least one isothiazolone compound of the formula

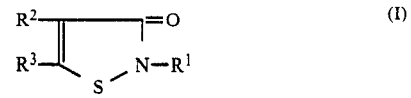

wherein $R^1$ is an alkyl group of from 1 to about 18 carbon atoms, and $R^2$ and $R^3$ are each independently H or a halogen, (C) from 60 to about 99% by weight of water, (D) from about 0.1 to about 20% of at least one surfactant, and (E) less than about 30% by weight of a hydrocarbon solvent.

21. A method of preserving wood which comprises contacting the wood with the composition of claim 11.

22. A method of preserving wood which comprises contacting the wood with the composition of claim 20.

23. Wood treated in accordance with the method of claim 21.

24. Wood treated in accordance with the method of claim 22.

* * * * *